(12) United States Patent
Lindman

(10) Patent No.: US 9,339,198 B2
(45) Date of Patent: May 17, 2016

(54) HEADPHONES MEASURING HEART-RATE

(71) Applicant: Suunto Oy, Vantaa (FI)

(72) Inventor: Erik Lindman, Vantaa (FI)

(73) Assignee: Suunto Oy, Vantaa (FI)

( * ) Notice: Subject to any disclaimer, the term of this patent is extended or adjusted under 35 U.S.C. 154(b) by 0 days.

(21) Appl. No.: 14/356,396

(22) PCT Filed: Nov. 6, 2012

(86) PCT No.: PCT/FI2012/051086
§ 371 (c)(1),
(2) Date: May 6, 2014

(87) PCT Pub. No.: WO2013/068644
PCT Pub. Date: May 16, 2013

(65) Prior Publication Data
US 2014/0323889 A1  Oct. 30, 2014

Related U.S. Application Data

(60) Provisional application No. 61/558,565, filed on Nov. 11, 2011.

(51) Int. Cl.
*A61B 5/024* (2006.01)
*H04R 1/10* (2006.01)
*A61B 5/00* (2006.01)

(52) U.S. Cl.
CPC ............. *A61B 5/02433* (2013.01); *A61B 5/024* (2013.01); *A61B 5/6803* (2013.01); *H04R 1/1091* (2013.01); *A61B 5/002* (2013.01)

(58) Field of Classification Search
CPC .. A61B 5/0205; A61B 5/7264; A61B 5/0533; A61B 5/1118; A61B 5/6801; A61B 5/7282; A61B 5/6803; A61B 5/486; A61B 5/6815; A61B 5/0402; A61B 5/0082; A61B 5/02427; A61B 5/14552; A61B 5/024; A61B 5/0006; A61B 5/0482; A61B 5/0484; A61B 7/00; A61B 2562/0204; A61B 2562/0233; A61B 5/00; A61B 5/04012; A61B 5/222; A61B 5/7405; A61B 5/02; A61B 5/6898; A61B 7/04; A61B 2562/227; A61B 5/6814; A61B 5/72; A61B 7/02; A61B 8/56; G06F 17/30743; Y10S 128/92; H04R 1/105; H04R 29/00; H04R 5/0335; A61M 2230/06; A61M 2205/3375; A61M 2205/581; A61M 2209/088; A61M 2230/04; G08B 21/0453; H04L 67/12; H04L 67/22
See application file for complete search history.

(56) References Cited

U.S. PATENT DOCUMENTS

2008/0076972 A1  3/2008  Dorogusker et al.
2009/0105548 A1  4/2009  Bart
2010/0262025 A1  10/2010  Hu et al.

*Primary Examiner* — Deborah Malamud
(74) *Attorney, Agent, or Firm* — Seppo Laine Oy

(57) ABSTRACT

The invention relates to headphones and a method for listening to music or some other audio signal, which headphones comprise at least one sound source such as a an earphone to be placed in the vicinity of the ear, for producing sound, and a galvanic conductor for feeding an electrical signal from a signal source, such as a music player or similar, to the sound source. In accordance with the invention at least one sound source is equipped with means for measuring heart rate, as well as means for forwarding heart-rate information wirelessly.

8 Claims, 1 Drawing Sheet

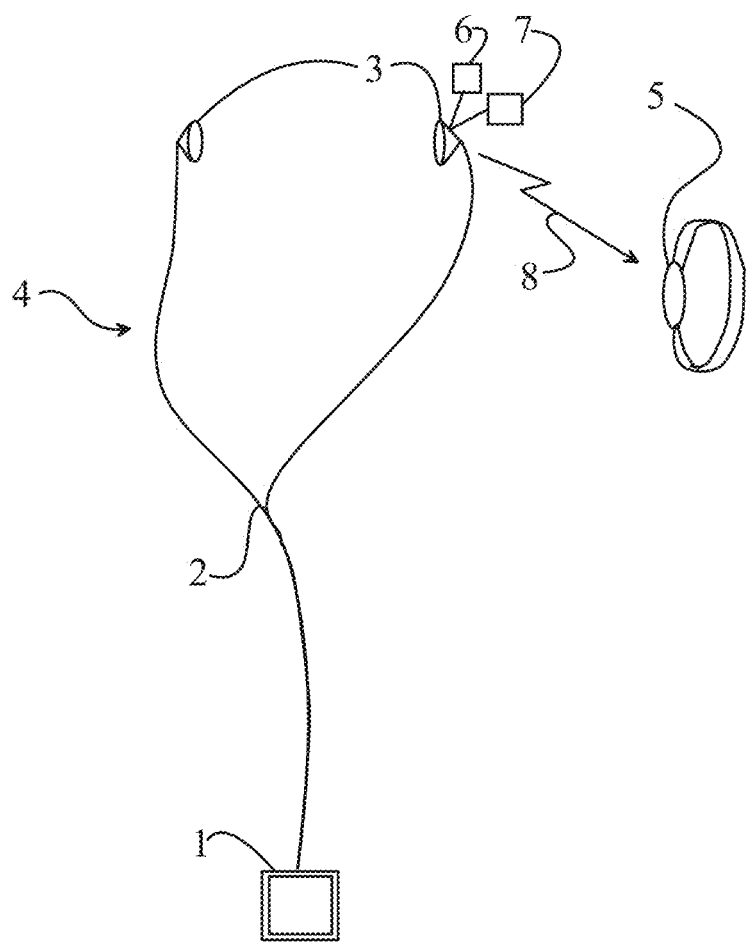

HEADPHONES MEASURING HEART-RATE

The invention relates to headphones measuring heart-rate, according to the preamble to Claim 1.

The invention also relates to a method.

According to the prior art, applications exist in which headphones, particularly earphones pushed into the outer auditory canal, are used to measure heart-rate using the same device that produces music for listening.

Both wired and wireless solutions are known. The wireless solutions are based on using Bluetooth technology and for this reason the devices are unavoidably too heavy to use during exercise. The power consumption of these wireless devices is also large.

The wired devices, on the other hand, are bound to a specific type of music player or telephone, so that wired headphones according to the prior art that measure heart-rate can only be used in connection with a specific device.

The invention is intended to eliminate at least some of the drawbacks of the prior art.

The invention is based on equipping wired headphones with both a unit that measures heart-rate, and a transmitter, by means of which heart-rate information can be sent wirelessly to a wristop computer.

According to one preferred embodiment of the invention, the transmission and heart-rate measurement units of the headphones receive their operating power from the audio signal of the headphones.

According to a second preferred embodiment of the invention, the measurement/transmission unit uses a battery as its power source, or at least a battery as a standby power buffer.

More specifically, the device according to the invention is characterized by what is stated in the characterizing portion of Claim 1.

The method according to the invention is, for its part, characterized by what is stated in the characterizing portion of Claim 7.

Considerable advantages are achieved by means of the invention.

The headphone unit measuring heart-rate is entirely independent of the music player or telephone being used. In other words, the music-player user need not synchronize the music library separately with the sports device; instead heart-rate measurement is effortlessly available in connection with a normal, familiar music device.

Thus, according to the invention, the device to which the headphones are wirelessly connected is a different device to that in which the heart-rate information is displayed. This device, which displays and/or receives heart-rate information, is typically a wristop computer.

The invention can be used in connection with any music player whatever, using any wireless heart-rate information receiver whatever. From the point of view of the heart-rate information reception, there is no difference whether a message comes from headphones or a heart-rate belt. This can even be implemented in such a way that, if a smart phone is available, then the music application, i.e. the 'player', is independent and the heart-rate application is independent. The author of the heart-rate application need not then be concerned about the music application, even if the applications are operating simultaneously in the same telephone.

One advantage of the invention is that wired headphones can be used with only the input energy of a music player, provided the heart-rate measurement solution and transmitter require a sufficiently small amount of energy.

This solution is light. The advantaged of a wired solution over a purely wireless one are lightness, price, and compatibility. The music transfer of an entirely wireless solution requires classic Bluetooth, which in turn demands a great deal of power and thus a heavy headphone solution (must be recharged frequently), which is uncomfortable, and in sports use often even unusable. In addition, in this case the player too must transmit music wirelessly, consuming a great deal of power.

A typical solution for the invention is probably one in which the heart-rate sensor and the transmitter have their own replaceable dry-cell or rechargeable battery. The battery is used only for heart-rate measurement and for low-power radio transmission, for example for sending a radio message using the Bluetooth low-energy-technology standard. Energy is not drawn from the battery to produce sound for music. The electronics of the headphones can be constructed to be separate; however in such a way that the switching on of the heart-rate measurement can be controlled by detecting the music state, so that when music can be heard the measurement is switched on. According to the invention, it is also possible to switch on the measurement manually.

The invention will be examined on the basis of the accompanying FIGURE, in which FIG. 1 shows a schematic diagram on one embodiment of the invention.

According to the invention, the headphones 4 consist of earphone-elements 3 acting as a sound source, which are connected by galvanic conductors 2 to a suitable device 1 producing music or speech, which can be an MP3-player, a telephone, or a tablet computer. In the present application, the device 1 is also referred to as a signal source. At least one of the earphone units contains an infrared measuring device 6, which is used, for example by means of the technique known from U.S. Pat. No. 6,080,110, to measure an infrared-range signal from the surface of the skin or through the skin and to convert the signal into heart-rate information. In other words, the reflection of the skin surface or a change in the emission properties is converted into heart-rate information. Radiation can be focused on the skin surface, or only the infrared radiation emitted by the skin can be measured. The signal is measured either from the outer auditory canal or the auricle, or through the auricle. The measured signal is transmitted 8 to a wristop computer by a transmitter 7 using a normal wristop-computer data-transfer protocol, either analogously or digitally wirelessly.

Power supply to the transmitter 7 and the measuring device 6 is implemented either by its own dry-cell or rechargeable battery, or by 'stealing' energy from the audio signal.

Instead of infrared measurement, the heart-rate measurement can be measured as a galvanic measurement using electrodes between the earphones 3.

The invention claimed is:

1. Headphones for listening to music or some other audio signal, which comprise
   at least one sound source configured to be placed in the vicinity of the ear, for producing sound, and
   a galvanic conductor for feeding an electrical signal from a signal source to the sound source, said sound source being equipped with means for measuring heart-rate, as well as means for forwarding heart-rate information wirelessly, and
   means for starting heart-rate measuremt once an audio signal fed to the headphones is detected.

2. Headphones according to claim 1, wherein the heart-rate measurement is implemented using infrared technology.

3. Headphones according to claim 1, wherein the heart-rate measurement is implemented from the outer auditory canal using infrared technology.

4. Headphones according to claim 1, wherein power supply to the measurement and transmission means is implemented using a dry-cell battery or rechargeable battery.

5. Method in headphones, comprising the steps of:
feeding a signal from a signal source to a sound source, with the aid of galvanic conductors,
equipping the sound source with means for measuring heart-rate, as well as means for forwarding heart-rate information wirelessly, and
starting heart-rate measurememt once an audio signal fed to the headphones is detected.

6. Method according to claim 5, wherein the heart-rate measurement is implemented using infrared technology.

7. Method according to claim 5, wherein the heart-rate measurement is implemented from the outer auditory canal using infrared technology.

8. Method according to claim 5, wherein power supply to the measurement and transmission means is implemented using a dry-cell battery or rechargeable battery.

* * * * *